United States Patent
O'Connor et al.

(10) Patent No.: US 6,536,477 B1
(45) Date of Patent: Mar. 25, 2003

(54) FLUIDIC COUPLERS AND MODULAR MICROFLUIDIC SYSTEMS

(75) Inventors: Stephen D. O'Connor, Pasadena, CA (US); Eugene Dantsker, Sierra Madre, CA (US); Christoph D. Karp, Pasadena, CA (US); Marci Pezzuto, Altadena, CA (US)

(73) Assignee: Nanostream, Inc., Pasadena, CA (US)

( * ) Notice: Subject to any disclaimer, the term of this patent is extended or adjusted under 35 U.S.C. 154(b) by 33 days.

(21) Appl. No.: 09/689,568

(22) Filed: Oct. 12, 2000

(51) Int. Cl.$^7$ ................................. F15C 1/06
(52) U.S. Cl. ................. 137/833; 422/100; 204/601
(58) Field of Search ................... 137/833, 803, 137/828; 251/368; 422/100, 101, 103; 204/600, 601

(56) References Cited

U.S. PATENT DOCUMENTS

| | | | |
|---|---|---|---|
| 3,568,692 A | * 3/1971 | Metzger et al. | 204/159.23 |
| 4,751,172 A | * 6/1988 | Rodriguez et al. | 204/478 |
| 5,839,467 A | * 11/1998 | Saaski et al. | 137/501 |
| 5,890,745 A | 4/1999 | Kovacs | 285/24 |
| 6,074,725 A | 6/2000 | Kennedy | 428/188 |
| 6,287,520 B1 | * 9/2001 | Parce et al. | 422/100 |
| 6,321,791 B1 | * 11/2001 | Chow | 137/833 |

FOREIGN PATENT DOCUMENTS

| | | | |
|---|---|---|---|
| DE | 197 39 722 | 4/1999 | H05K/3/36 |
| WO | WO 99/19717 | 4/1999 | G01N/25/22 |
| WO | WO 99/60397 | 11/1999 | G01N/33/483 |

OTHER PUBLICATIONS

Gray, B., "Novel interconnection technologies for integrated microfluidic systems," Sensors and Actuators 77 (1999) 57–65.

Schuenemann, M. et al., "A highly flexible design and production framework for modularized micromechanical systems," Sensors and Actuators 73 (1999) 153–168.

Ehrfeld, W. et al., "Potentials and Realizations of Microreactors," Dechema Monographs vol. 132 (1996).

van der Schoot, B. et al., "A modular miniaturized chemical analysis system," Sensors and Actuators B, 13–14, (1993) 333–335.

Yao, T. et al., "Micromachined Rubber O–ring Micro–fluidic Couplers," 13th IEEE International Conference on Micro Electro Mechanical Systems (MEMS '00), Miyazaki, Japan, Jan. 23–27 (2000); http://touch.caltech.edu/publications/yao/mems00/mems00.pdf.

Gonzalez, C. et al., "Fluidic interconnects for modular assembly of chemical microsystems," Sensors and Actuators B 49 (1998) 40–45.

* cited by examiner

Primary Examiner—A. Michael Chambers
(74) Attorney, Agent, or Firm—Vincent K. Gustafson; Michael F. Labbee (57) ABSTRACT

Microfluidic coupling devices capable of connecting more than one microfluidic module together to form a larger, integrated system are described. These devices are constructed in a number of ways. In a certain embodiments, the coupler is constructed from laminated materials and mates to one or more microfluidic devices using adhesive. The device can be used to place fluid into a microfluidic device, to remove fluid from a microfluidic device, or to transfer fluid between two or more microfluidic devices. Also described are modular microfluidic systems formed from microfluidic modules made using various techniques and/or useful for performing various functions.

49 Claims, 6 Drawing Sheets

FLUIDIC COUPLERS AND MODULAR MICROFLUIDIC SYSTEMS

FIELD OF THE INVENTION

The present invention relates to microfluidic devices and particularly to integration of modular microfluidic systems, and microfluidic devices for introducing fluid into another microfluidic device and for removing fluid from a microfluidic device.

BACKGROUND OF THE INVENTION

There has been a growing interest in the manufacture and use of microfluidic systems for chemical and biochemical manufacturing processes and the acquisition of chemical and biological information. In particular, microfluidic systems allow complicated biochemical reactions to be carried out using very small volumes of liquid. These miniaturized systems increase the response time of the reactions, minimize sample volume, and lower reagent cost.

Traditionally, these microfluidic systems have been constructed in a planar fashion using photolithography to define channels on silicon or glass substrates and etching techniques to remove material from the substrate to form the channels. More recently, a number of methods have been developed that allow microfluidic devices to be constructed from plastic, silicone or other polymeric materials. Finally, novel microfluidic devices are described in co-pending U.S. patent application Ser. Nos. 09/453,026 and 09/453,029. These devices comprise one more stencils containing microstructures, which are disposed and sealed between substrate layers.

Thus, several different types of microfluidic devices, manufactured using several different techniques exist. For example, a preparation system could be constructed using silicon fabrication technology while a sorting device might be constructed using a silicone replication technique (see, Fu et al., Nature Biotechnology (199) 17: 1109–1111). In this situation, it would be impossible to develop a single integrated device.

Therefore, a great need exists for a device or method for connecting together different types of microfluidic devices that may have been manufactured using different techniques.

Moreover, discrete microfluidic components are often constructed that only perform partial functions of a complete system and there is a need to integrate such devices. For example, a silicon based microfluidic sample preparation system can be constructed. A separate microfluidic detection system could also be constructed. To make a completed device, the developer must typically go back to the development stage and develop processing techniques and steps that allow a single-integrated device to be developed.

Another issue in the development of microfluidic systems is the manner in which fluids and samples are injected into the device and removed from the device, which can often be a limiting problem with these devices.

SUMMARY OF THE INVENTION

The present invention provides a coupling device capable of connecting more than one microfluidic module together to form a larger, integrated system. It also provides a modular system of microfluidics components that can be combined in various configurations to construct completed microfluidic multichip modules (MMCMs) or modular microfluidic systems. In this manner, prototyping and manufacturing can be accomplished in a very rapid manner, since a complete set of building blocks can be constructed in bulk.

Further, the present invention provides a robust microfluidic coupling device for inputting fluids into a microfluidic device and removing fluids from those devices. These devices can be incorporated into existing industrial equipment.

Additionally, the present invention provides a microfluidic coupling device where the fluids within a microfluidic device can be transported off the device and easily manipulated. Microfluidic couplers of the present invention also allow a small amount of fluid to be removed from a microfluidic device with minimal loss of sample during the process.

Moreover, the invention provides a microfluidic coupling device that can accommodate the use of a vast array of liquid reagents or solutions. Different types of solvents and samples can be used, including but not limited to water based systems, organic based systems, biological materials solvated or dispersed within solvent, chemical systems, and others known by those skilled in the art. The microfluidic coupling devices of the present invention are constructed using a combination of traditional manufacturing techniques and novel chemistries and alignment procedures.

The present invention also incorporates electrodes into microfluidic coupling devices to perform electrokinetic flow, electrophoresis, and/or electronic detection within the devices.

Definitions

The term "channel" or "chamber" as used herein is to be interpreted in a broad sense. Thus, it is not intended to be restricted to elongated configurations where the transverse or longitudinal dimension greatly exceeds the diameter or cross-sectional dimension. Rather, such terms are meant to comprise cavities or tunnels of any desired shape or configuration through which liquids may be directed. Such a fluid cavity may, for example, comprise a flow-through cell where fluid is to be continually passed or, alternatively, a chamber for holding a specified, discrete amount of fluid for a specified amount of time. "Channels" and "chambers" may be filled or may contain internal structures comprising valves or equivalent components.

The term "microfluidic" as used herein is to be understood, without any restriction thereto, to refer to structures or devices through which fluid(s) are capable of being passed or directed, wherein one or more of the dimensions is less than 500 microns.

"Substantially planar" as used herein refers to a structure having a height of between about 1 and 500 microns and a length and width each at least 100 times larger than the height.

A "stencil layer" as used herein refers to a discrete layer of material through which a channel or aperture has been cut, such that in the final device, the top and bottom surfaces of the microfluidic channel within the stencil layer are, formed from the bottom and top, respectively, of adjacent stencil or substrate layers. The stencils are preferably sandwiched between substrates, wherein the substrates are preferably substantially planar. Stencil layers are bonded by any technique that results in substantially liquid-tight channels within the device.

BRIEF DESCRIPTION OF THE DRAWINGS

FIG. 1 is two figures of two types of microfluidic coupling devices.

FIG. 2 is a schematic of a microfluidic metering device with three microfluidic coupling devices at the outputs of each metering channel.

FIG. 3 is a schematic of two microfluidic devices being coupled with microfluidic couplers at the outputs.

FIG. 4 is a schematic of a system using the microfluidic couplers as input devices.

FIG. 5 is a schematic of an MMCM system that incorporates electrodes.

DETAILED DESCRIPTION OF THE INVENTION

This invention describes modular microfluidic systems and microfluidic coupling devices that are used to connect microfluidic modules and to transport fluid into a microfluidic device, bring fluid off of a microfluidic device, or transfer fluid between two devices.

Figure 1A:
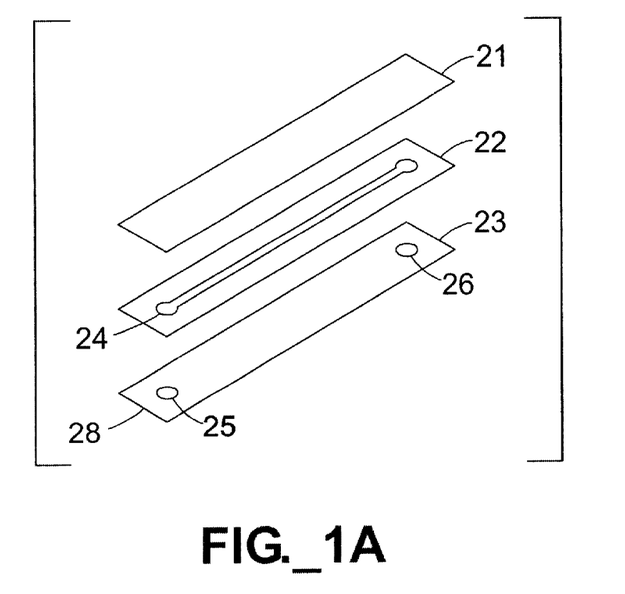
Figure 1B:
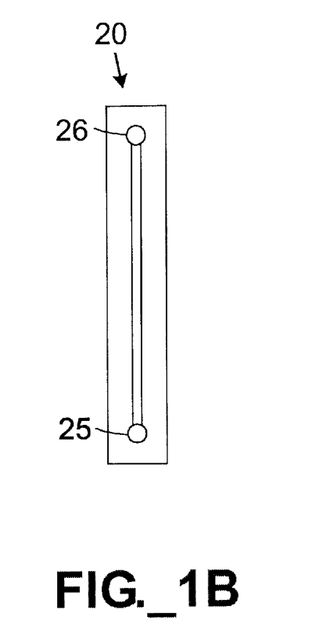

Referring to FIG. 1A, the invention provides a microfluidic coupling device having a substantially planar first substrate layer 21 and a substantially planar second substrate layer 23. The second layer has a lower surface which defines the bottom of the microfluidic coupling device. The coupling device also has at least one substantially planar stencil layer 22 disposed between the first and second substrate layers. The stencil layer has at least one channel 24 formed in it, with at least one dimension less than about 500 microns. The channel is in fluid communication with a first aperture 25 or second substrate layer. The channel must be vented to allow fluid to flow. Although not required in all cases, the device of FIG. 1A contains a second aperture 26 in the second substrate layer. The second aperture 26 is in fluid communication with the channel 24. In some embodiments, the second aperture is in the first substrate layer. Alternatively, all or a portion of either substrate layer can be a semipermeable membrane that allows gas to pass, but substantially prevents liquids from crossing.

For devices of the type shown in FIG. 1, adjacent surfaces of stencil layers and substrate layers and, where applicable, between stencil layers, are complementary so as to form a seal with the sandwiched stencil. Most preferably, the mating substrates are substantially planar. The stencils and substrate layers can be constructed from any suitable materials, including preferably MYLAR™, polyester, polyimide, (e.g., KAPTON™) and adhesive tapes. One or more materials are preferably used to coat, seal, and/or adhere the channels formed between the substrates. Where the layers are constructed from adhesive tapes, the tapes can be temperature curing tapes, chemically curing tapes, optical curing tapes, and other types of curing tapes. The stencil and substrate layers may be stacked or layered to provide a complex microfluidic device.

In one embodiment, the stencil layers are comprised of single- or double-sided adhesive tape. A portion of the tape (of the desired shape and dimensions) can be cut and removed to form, for example, a channel 24 or entry/exit ports 25,26. The tape stencil can then be placed on a supporting substrate or between layers of tape. In one embodiment, stencil layers can be stacked on each other. In this embodiment, the thickness or height of the channels can be varied by simply varying the thickness of the stencil (e.g., the tape carrier and the adhesive or glue thereon).

In certain embodiments, double sided tape can be used to construct the devices. In this embodiment, various substrate materials can be used for the other stencil layers. For example, in one example stencil layer 21 is constructed from a MYLAR® material, stencil layer 22 from double sided tape and stencil layer 23 from single sided tape with a MYLAR® backing. In this manner, the top and bottom layer of the channel 24 are both MYLAR® material.

In a preferred embodiment, adhesive is used to connect the devices. In a more preferred embodiment, the adhesive surface used to couple the microfluidic coupler to the microfluidic device is a non-permanent adhesive. In this manner, the device can be connected to the device, the fluid added, and the microfluidic coupler can then be removed.

In another preferred embodiment, the surface used to couple the microfluidic. coupler to the microfluidic device is a tacky surface such as silicone.

In one embodiment, the microfluidic coupling device is flexible. The entire device can be constructed of various films, papers, tapes, plastics and the like such that the coupling device is flexible. Flexibility can aid in alignment of the microfluidic coupling device to another microfluidic device or can facilitate coupling another fluidic device to a microfluidic device. The material used also can be malleable. Such malleability aids in sealing the microfluidic coupling device with another device, especially in cases where the mating surface of the other device is uneven.

The microfluidic device of FIG. 1A can be constructed such that the lower surface of the second substrate 23 is adhesive and one, or more of the apertures connects through the second substrate. The device also can be constructed such that the upper surface of the first substrate layer 21 is adhesive. In one embodiment, the device has two apertures, one in the first substrate layer and one in the second substrate layer, and both the upper surface and lower surface are adhesive. Such an embodiment allows for rapid connection of the coupling device to other microfluidic devices. The adhesive used can be a permanent adhesive or can be a removable adhesive. In such an embodiment, the device also can include a backing layer removably adhered to the adhesive lower surface of the second substrate 23. The backing material protects the adhesive material until such a time as the microfluidic coupling device is to be attached to another microfluidic device. The backing material can be any suitable plastic, paper or foil.

Figure 1C:
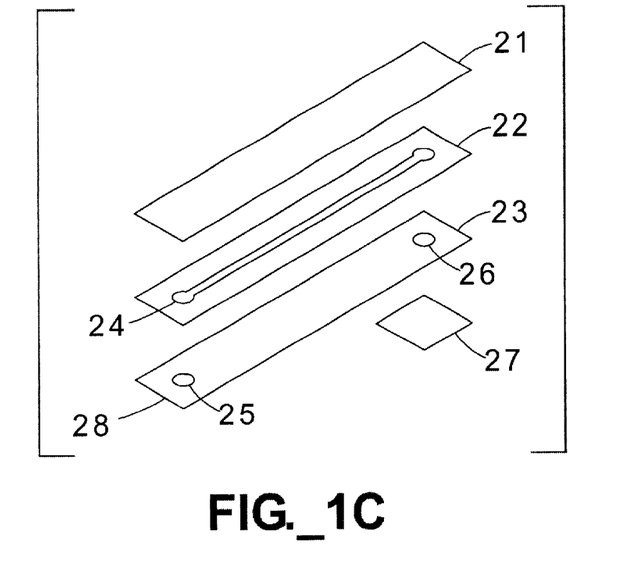
Figure 1D:
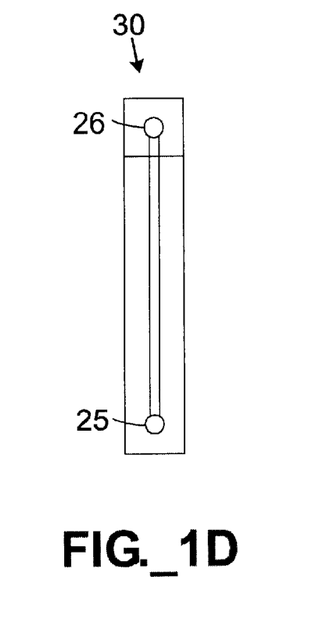

The microfluidic device of the invention also can include a semipermeable membrane 27 covering the second aperture 26, as shown in FIG. 1C. The semipermeable membrane 27 allows gases to pass, but will not substantially allow a liquid to pass. For example, a suitable semipermeable membrane will allow air to pass through it, but will not allow water to pass. A suitable semipermeable membrane can have pores of a sufficient size to achieve the desired effect. In one embodiment, the semipermeable membrane is a polymeric material with a pore size of less than about 75 microns, and preferably less than about 10 microns. Examples of such filter materials include X-7744, a 7 $\mu$m pore size T3 sheet from Porex Technologies (Fairburn, Ga.) and GORETEX®-type materials.

In one embodiment, the first aperture of the microfluidic device shown in FIG. 1A is used as an inlet port, and the second aperture is used as a vent for air escape. Alternatively, the second aperture can be used as an exit port rather than a vent. The inlet port can be directly coupled to another microfluidic device using adhesive. The adhesive can either be on the coupling device or on the microfluidic device to which the coupling device is to be attached.

In another preferred embodiment, porous materials can be used at the outlet of the microfluidic coupler to add impedance to the system. These materials can be chosen so that their properties are such that they have slight resistances to air or gas, and very large resistances to fluid flow. The pore size and material composition can be selected to produce the desired effects and impedances. Different materials can be used at various outlets. In this manner, the outlet materials can be used in conjunction with the overlap impedances to produce preferential fluid flow within a device. Microfluidic devices with impedances are described in co-pending U.S. application Ser. No. 09/550,184 which is incorporated herein by reference.

In a preferred embodiment, the bottom surface 28 of the microfluidic coupler near the inlet port 25 is covered with an adhesive material that allows the inlet port to be connected to the outlet port of a microfluidic device. Alternatively, the surface 28 can be non-adhesive and the surface of the microfluidic device to be coupled to can be adhesive. In an alternative embodiment, both surfaces are adhesive.

The adhesive can be placed on the outer surface of the microfluidic device 28 in a number of ways. In a preferred embodiment, the bottom surface 28 of stencil layer 23 is inherently adhesive. In other embodiments, a coating is placed on the bottom surface 28 either before or after assembly. This coating can be accomplished in a number of ways, including spin coating, spray coating, etc.

The microfluidic devices of the present invention also provide for lowering the standard deviation of a given process when the amount of fluid is small and unknown. An unknown amount of fluid can be injected into a microfluidic device. The device can meter off a known quantity of sample with very low standard deviation and then transport the fluid off board for further analysis.

In certain embodiments, it may be desirable not to have the outlet port be open to the environment. Also, in some embodiments, the microfluidic coupling device can have a flap of material for sealing either the first or second aperture. In a preferred embodiment, an aperture is in the lower surface and the surface is adhesive, and the flap is an extension of the second substrate.

The channels within the microfluidic couplers of the invention can also be designed wherein the channels are derivatized with a chemical or biological moiety in order to perform a binding or separation function. Referring, to FIG. 1A, the microfluidic coupler 20 has a stencil layer 21, which is constructed from thin sheets of glass that are ¼" by 1½" by ¹⁄₃₂". The stencil layer 22 is made from 3.4 mil thick double sided tape with a 40 mil wide channel. Finally, a single sided piece of adhesive forms stencil 23 with 0.08" diameter inlet/outlet holes 25,26. Prior to assembling, the glass stencil 21 is derivatized using a typical silization reaction. Genetic probes can then be bound to the surface of the glass.

In operation, a sample is manipulated within a microfluidic module (not shown) and passed into the microfluidic coupler 20. The sample can contain labeled genetic stands of interest that may bind to the surface of the derivatized glass. After incubation, the channel of the microfluidic coupler 20 can be washed to remove non-specific binding. The surface of the channel can then be analyzed to determine if the labeled genetic material of interest is present. For instance, the genetic samples may be fluorescently labeled and the fluorescence of the channel studied.

Other types of surface chemistry can also be utilized, such as anti-body binding to polystyrene or Teflon or other materials.

The invention also provides for modular microfluidic system made from a plurality of microfluidic modules. Each module is adapted for rapid attachment to or detachment from one or more other modules, and is self-contained for performing a desired function independently of each other module. In a preferred embodiment, the microfluidic modules are attached to each other using the microfluidic couplers shown in FIG. 1. As would be obvious to one of ordinary skill in the art the microfluidic modules may have one or more fluid inlets and one or more fluid outlets. In a preferred embodiment, these modular microfluidic systems can be made from modules which perform chemical or biochemical synthesis or chemical or biochemical analysis. The modular systems are also designed for use in either continuous processing mode or in batch processing mode.

Microfluidic modules for use with the modular microfluidic systems may be constructed using photolithography to define channels on silicon or glass substrates and etching techniques to remove material from the substrate to form the channels. Manz et al. (Trends in Anal. Chem. (1990) 10(5): 144–149; Advances in Chromatography (1993) 33: 1–66). Miniature pumps and valves can also be constructed to be integral within such modules. Alternatively, separate or off-line pumping mechanisms are contemplated. Microfluidic modules can also be constructed from plastic, silicone or other polymeric materials by, for example, first constructing a negative mold and then pouring plastic or silicone into or over the mold. The mold can be constructed using a silicon wafer (see, e.g., Duffy et al., Analytical Chemistry (1998) 70: 4974–4984; McCormick et. al., Analytical Chemistry (1997) 69: 2626–2630), or by building a traditional injection molding cavity for plastic devices. Additionally, microfluidic modules may be constructed using a lithography, electroplating and molding technique (LIGA) technique developed at the Karolsruhe Nuclear Research center in Germany (see, e.g., Schomburg et al., Journal of Micromechanical Microengineering (1994) 4: 186–191), and commercialized by MicroParts (Dortmund, Germany). Microfluidic modules are also made using imprinting methods in PMMA (see, Martynova et. al., Analytical Chemistry (1997) 69: 4783–4789). Further, microfluidic modules can be constructed from stencil layers sandwiched between substrate layers as described in co-pending U.S. patent application Ser. Nos. 09/453,026 and 09/453,029.

The microfluidic modules are also capable of being used with a variety of pumping and valving mechanisms, including pressure, peristaltic pumping, electrokinetic flow, electrophoresis, vacuum and the like. In addition, the microfluidic modules are capable of being used in conjunction with optical detection (e.g., fluorescence, phosphorescence, luminescence, absorbance and colorimetry), electrochemical detection, and any of various suitable detection methods. Suitable detection methods will depend on the geometry and composition of the device. The choice of such detection methods will be within the purview of the skilled artisan.

Within the existing technology, a microfluidic device performs a function on a sample and once that function is completed, it is necessary to transport the fluid off the device for further analysis. In a preferred embodiment of the present invention, a microfluidic multi-chip module (MCM) is constructed that is capable of transporting samples between more than one microfluidic device.

In one embodiment, the invention provides microfluidic coupling devices that are used to capture fluid that has been manipulated in a microfluidic device and which can then be analyzed or manipulated in a larger laboratory experiment. FIG. 2 is a schematic of a microfluidic device that brings in a quantity of sample that has a large standard deviation, meters a known amount with a smaller standard deviation, divides the metered amount into three equal components, and brings the sample off-board for further analysis using the microfluidic couplers.

Figure 2A:
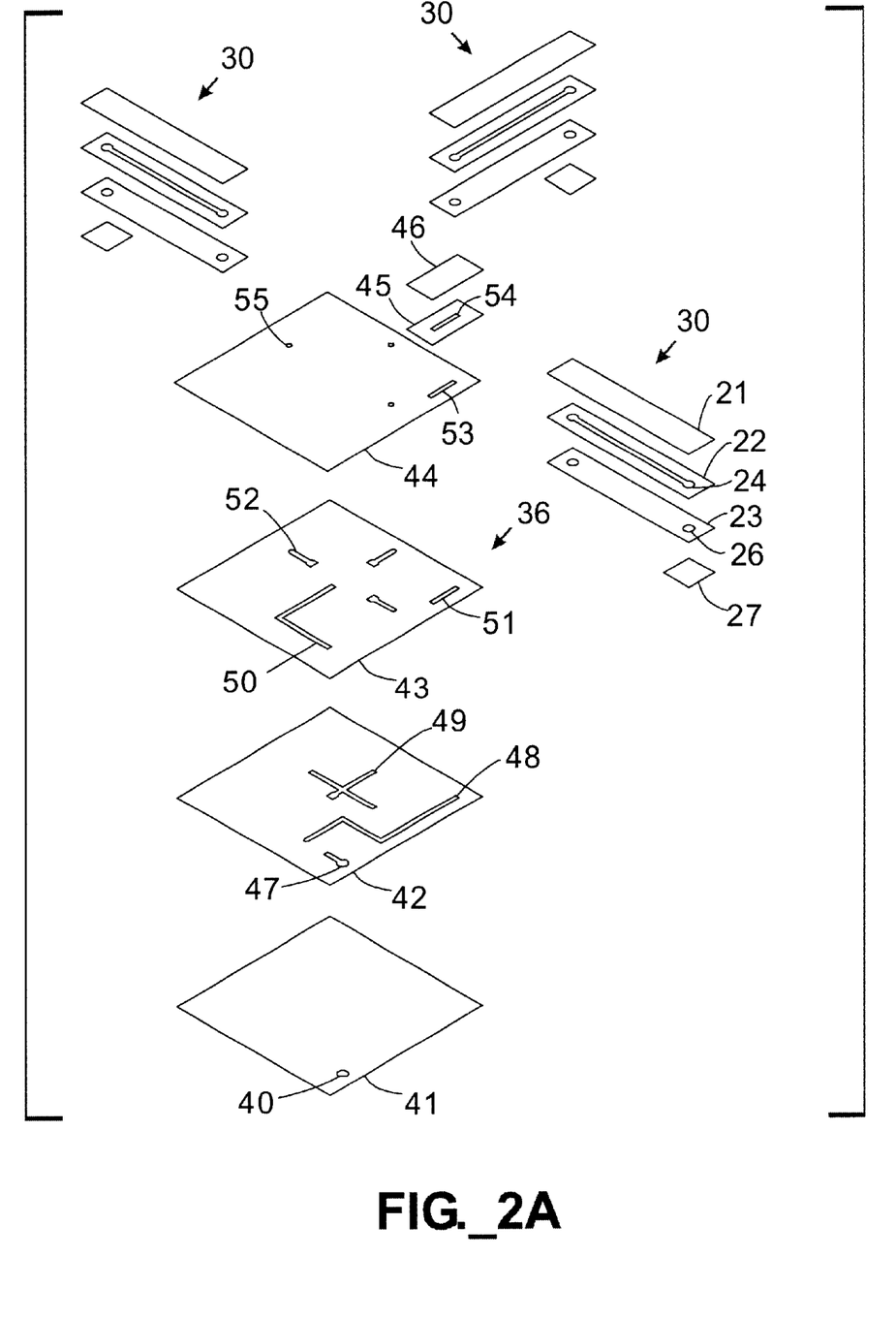

Referring to FIG. 2A, inlet port 40 is in a ⅛" thick polycarbonate base 41. Five stencil layers 42–46 have channels 47–54 cut into them. Additionally, outlet ports 55 are in one of the stencils 44. Single sided pieces of tape that consist of 3 mil (76 micron) polypropylene backing with permanent water based adhesive are used as the stencil material. Stencil layer 45 is constructed from double sided tape (0.5 mil thick polyester backing with acrylic adhesive on both sides) and stencil layer 46 is constructed from porous material (30–60 micron pore size PTFE, Norton A-125). The stencil layers are adhered together and onto the base.

The three microfluidic couplers 30 are constructed using three stencil layers 21–23 made from single sided tape (3 mil thick polypropylene with water based adhesive). The devices are 0.25" by 1⅜" in dimension. A channel 24 that is 0.04" wide and 1⅛" long is cut into stencil 22 and inlet and outlet holes 26 are cut into stencil 23 (holes are 0.08" in diameter). Stencil 27 is made from Norton G115 (1–2 micron pore size PTFE) cut to ¼" by ¼". All four stencil layers 21–23, 27 are adhered together to form the final microfluidic couplers.

Figure 2B:
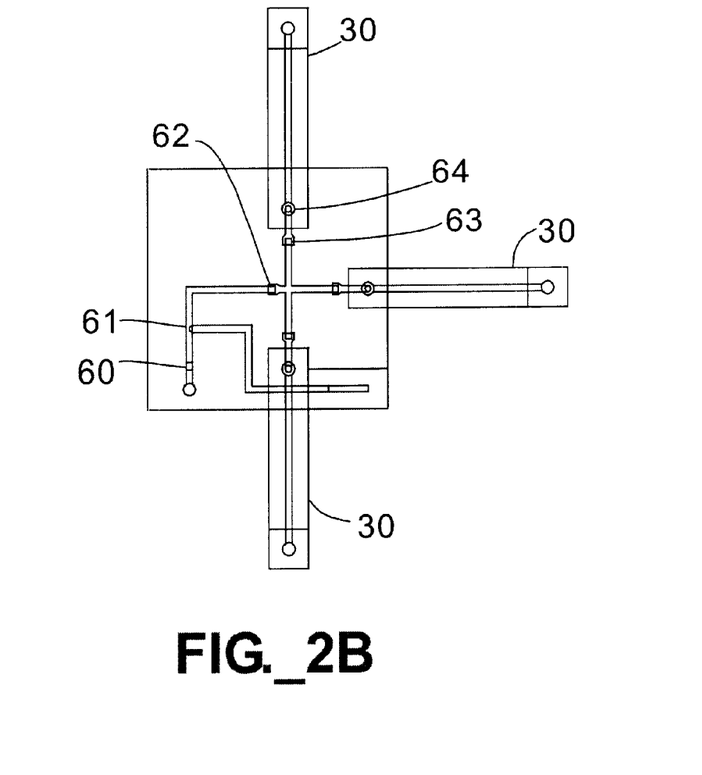

The assembled device is shown in FIG. 2B and contains four different types of overlap regions 60–64. All of the channels are 3 mils high, thus the overlap regions are 6 mils high. At overlap 60, both channels are 40 mils wide and they overlap for 40 mils. At overlap 61, channel 48 is 40 mils wide and tapers down to 20 mils in the overlap region; channel 50 is 40 mils wide and channel 48 extends across 50 for 20 mils. Overlaps 62 and 63 are identical. The entry channels 48, 49 are 40 mils wide, the exit portions are 70 mils wide and the overlap is 40 mils in length. The inlets 25 of the microfluidic couplers 30 are placed on top of the outlet ports of the device 55 and the adhesive tape on the bottom surface of the microfluidic couplers is used to seal the junction 64.

In operation, a sample plug is injected at the inlet port 40 using a syringe pump at a constant flow rate. A fluidic impedance 60 is constructed immediately after the inlet to control the initial fluid flow. The fluid then passes into channel 50 and fills the channel until it reaches impedance 62. At this point, the excess fluid within the sample breaks through the microfluidic impedance at 61 before the microfluidic impedance at 62. The excess fluid passes down channel 48. Once all of the excess fluid has passed into the waste channels (48, 51 and 54) it reaches the porous material 46. The fluid will not pass the porous material 46 and the microfluidic impedance 62 is overcome. The amount of sample now ready for further manipulation is defined by the volume of channel 50 between the two microfluidic impedances 61 and 62. If a different sample volume is desired, the microfluidic impedance 61 can be moved along channel 50 to alter the volume.

Once the air in channel 48 has been compressed sufficiently to build up enough pressure, microfluidic impedance 62 is overcome. The sample now enters chamber 49 and fills the entire chamber up to the impedances 63. Once this chamber has been completely filled, the output microfluidic impedances 63 are overcome and the samples enter into the inlet ports 55 of the microfluidic couplers 30 and enter into the channels 24 of the microfluidic couplers. Once all of the couplers 30 are filled, the couplers 30 can be removed and the samples within the couplers can be analyzed with an "off board" technique, such as scintillation counting (e.g., for $^{32}P$ labeled biomolecules) or fluorescence analysis.

In another embodiment, the invention provides for a device that uses a set of couplers to bring fluid from a metering manifold onto a filtering manifold, a second set of couplers to control fluid flow and a third set of couplers to transport the fluid off the device for further analysis.

Figure 3A:
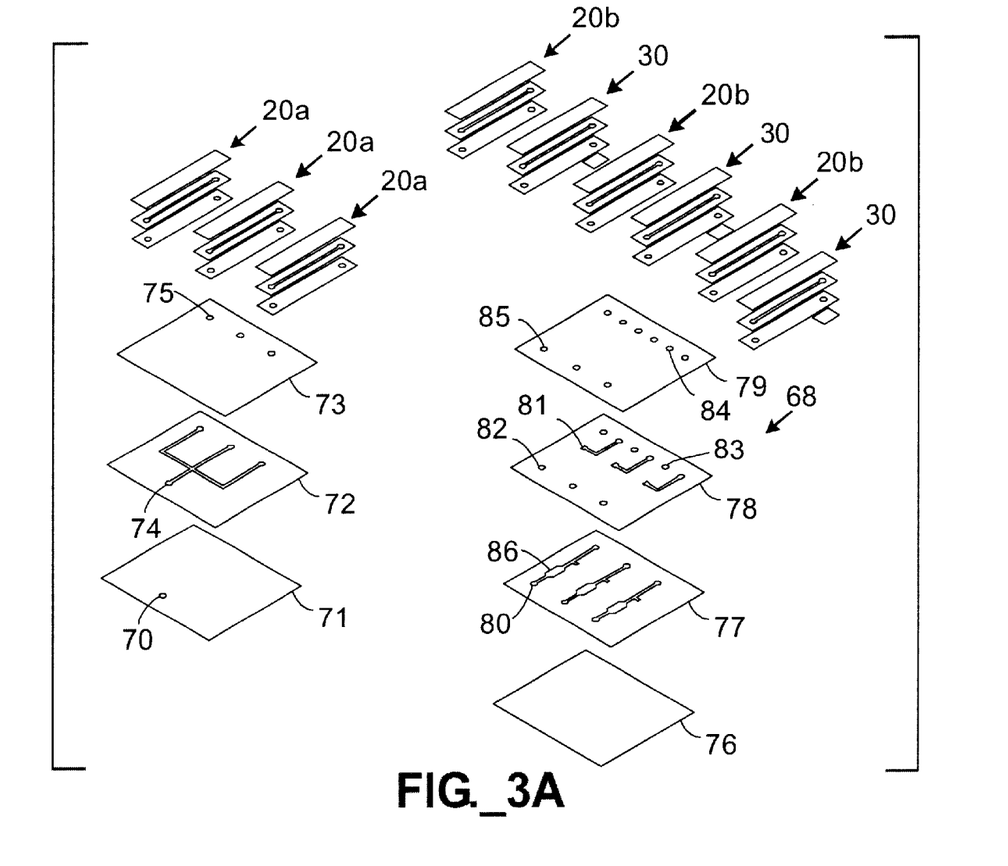

Referring to FIG. 3A, a ⅛" thick polycarbonate base 71 has an inlet port 70. Two stencil layers 72,73 have channels 74 and exit ports 75 cut into them. Single sided pieces of tape that consist of 3 mil (76 micron) polypropylene backing with permanent water-based adhesive are used as the stencil material. The channel 74 is 500 microns wide and the outlet ports 75 are 0.08" diameter. The stencil layers are adhered together and onto the base 71.

Similarly, another device is created by adhering three stencil layers 77–79 onto a ⅛" thick polycarbonate base 76. The stencils have channels 80,81, through-holes 82,83, inlet ports 85 and outlet ports 84 cut into them. All of the holes are 0.08" in diameter.

The microfluidic couplers 30 are identical to those shown in FIG. 2. The microfluidic couplers 20a, 20b are identical to the microfluidic couplers 30 with the exception that no porous material was added.

Figure 3B:
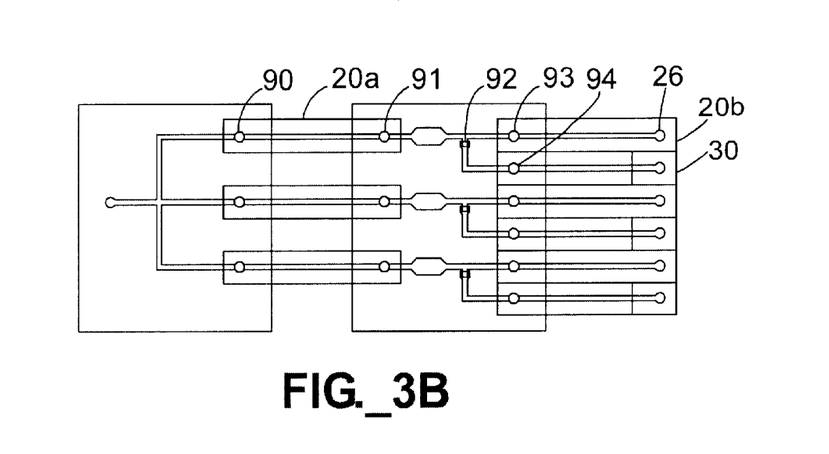

The assembled device is shown in FIG. 3B and contains five different types of overlap regions 90–94. At overlap region 90 fluid passes from the splitter device into the microfluidic coupler 20a. At overlap region 91 fluid passes from the microfluidic coupler into the filter manifold. Overlap region 92 is where two channels 80 and 81 overlap within the microfluidic device. At overlap region 93 fluid passes from the microfluidic device into the control microfluidic coupler 20b. At overlap region 94 fluid passes from the microfluidic device into the capture microfluidic coupler 30.

In operation, a sample plug is injected at the inlet port 70 using a syringe pump at a constant flow rate of 5 microliters per minute. The fluid then passes into channel 74 and is split into three outlets 75. The fluid enters the microfluidic couplers 20a and is transported to the inlet ports 85 of the second device. The fluid passes across the filter region 86, bypasses the overlap region 92 and is transported to the exit region 93 into the control microfluidic couplers 20b. In the embodiment shown, the filter region 86 does not contain any filter material. Once sufficient fluid has passed into the control microfluidic coupler, sufficient pressure is applied to the outlet 26 to increase the pressure within the device and overcome the impedance 92. The fluid then passes into the elution channel 81 and passes into the capture microfluidic coupling device 30. Once sufficient fluid has entered the capture microfluidic couplers 30 the devices can be removed from the main microfluidic device for further analysis. The output port 26 can be blocked by folding the device back on itself to cover the outlet port 26.

Figure 4A:
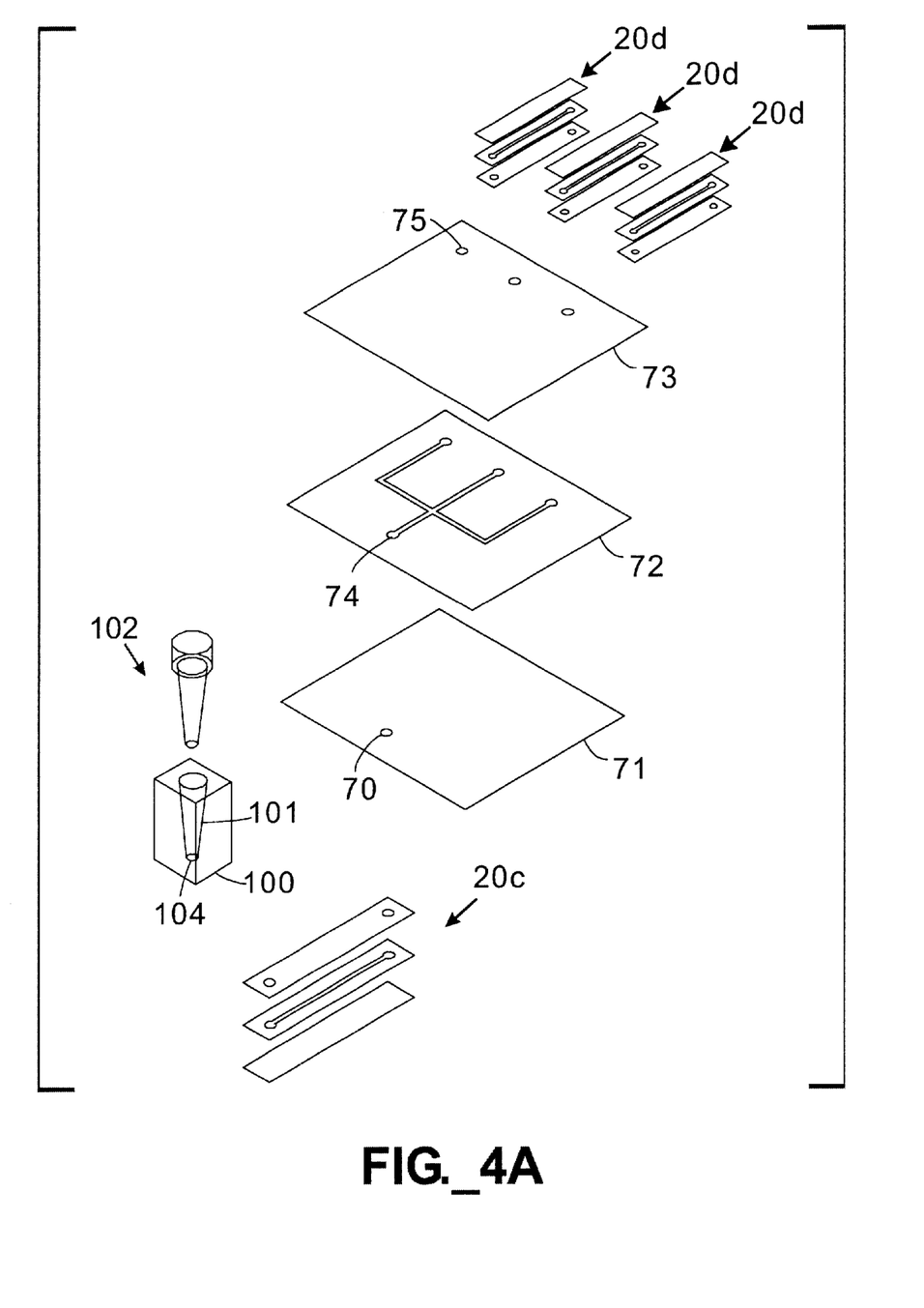

The microfluidic couplers of the invention can be used to input fluids into a device and export the fluid off the device. Referring to FIG. 4A, a microfluidic division device is constructed in the same manner as the device shown in FIG. 3. Also shown are couplers 20c and 20d, which are similar to the couplers 20b of FIG. 3. A pipette tip coupling block 100 that has a tapered hole 101 and is connected to the coupler 20c and is shaped to fit a standard pipette tip 102 snugly.

Figure 4B:
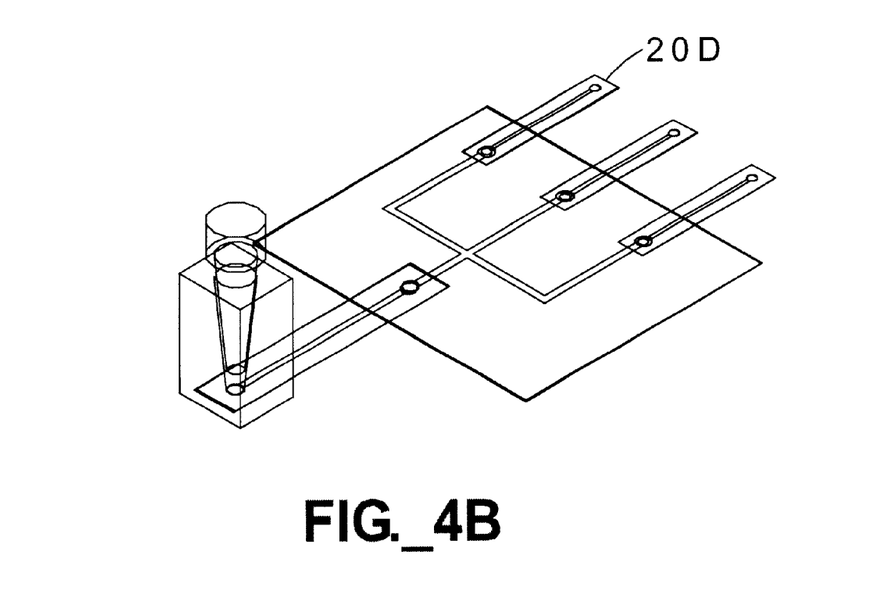

The assembled device is shown in FIG. 4B. In use, the microfluidic coupler 20c is flipped upside down and the inlet port is connected to the outlet port 104 of the pipette tip coupling block 100. The outlet port of the microfluldic coupler 20c is connected to the inlet port 70 of the distribution microfluidic device. The pipette tip is filled with the liquid and inserted into the pipette tip coupling block 100.

Fluid is injected into the device and passes through the outlets 73 into the output microfluidic couplers 20*d*. Then, the microfluidic coupler 20*c* can be removed from the pipette tip coupling block 100 and another device can be connected to the coupling block 100 in a similar manner.

In other versions of this embodiment coupling blocks can be constructed wherein fluid may be input using various methods, e.g., capillary tubes. In certain embodiments, a negative pressure can be applied at the outlet ports 75 of the microfluidic device to draw the fluid into the microfluidic coupler 20 and into the device. In certain embodiments, small aliquots of fluid can be inputted in this manner.

Figure 5A:
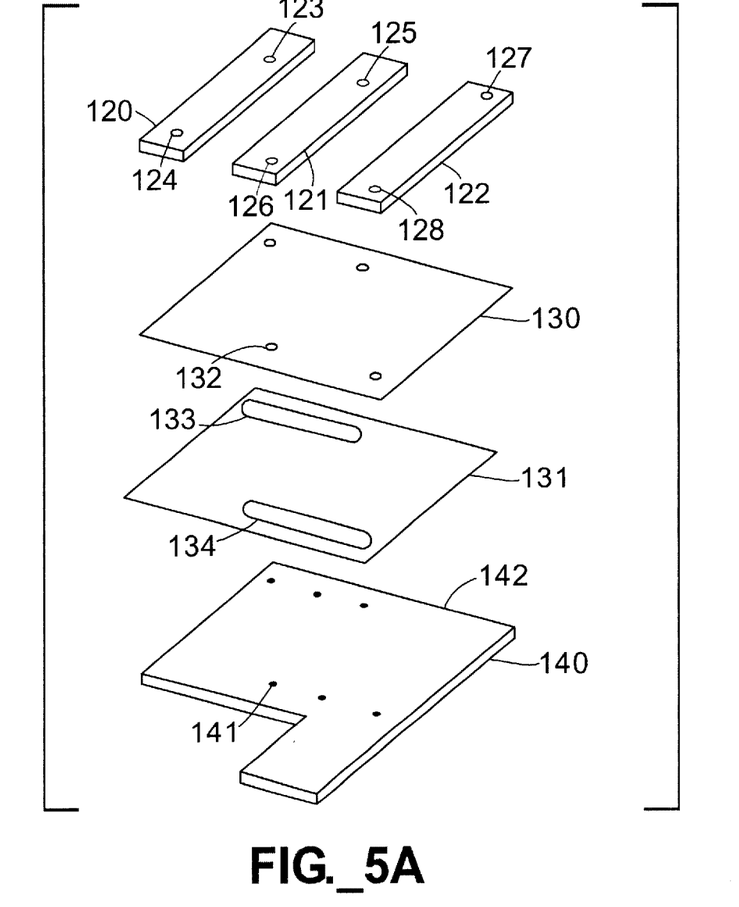

In a further embodiment, the invention is a microfluidic multi-chip module (MCM) that contains electrodes to perform various types of detection and or electroactive manipulation. Referring to FIG. 5A, a microfluidic MCM is constructed that is capable of joining three distinct microfluidic modules 120–122. These modules could be constructed from any number of different manufacturing techniques including silicon, silicone replications, hot embossing, molding, injection molding, etc. These modules can perform any number of fluidic functions. Microfluidic module 120 has an inlet port 123 on the bottom side and an exit port 124 on the top side. Microfluidic module 121 has both inlet port 125 and exit port 126 on the bottom side. Microfluidic module 122 has an inlet port 127 on the top side and an exit port 128 on the bottom side.

A microfluidic MCM that contains electrodes has a base 140, which is constructed using circuit board technology. The top surface 142 of the circuit board substrate forms the bottom layer of the microfluidic channels. Electrodes are placed at the entry of each channel and in the center of the MCM channels. The electrodes 141 are made by forming holes in the circuit board laminate where the electrodes are to be located, the substrate is then soaked in a copper solution, which covers the inside surfaces of the holes, the bottom and top surfaces are patterned and etched to form copper lines on the bottom side 144 and electrodes 141,143 on both sides, and a conductive epoxy is then screened into the holes that are to form the electrodes 141. Gold is then plated onto the electrodes 141 to form a well-defined electrode surface and the edges of the electrodes 141 are covered with a layer of solder mask, if so desired. In this manner, the top layer 142 can actually be the solder mask rather than the circuit board substrate itself.

The stencil layer 131 is constructed from single sided tape (2 mil polyester backing with acrylic adhesive) and has two channels 133,134 cut into it. The stencil layer 130 is made from double sided adhesive (0.5 mil polyester backing with acrylic adhesive on both sides) and has various inlet/outlet ports 132. The microfluidic MCM is assembled by adhering the two stencil layers onto the circuit board base 140. The microfluidic modules 120–122 can then be adhered to the MCM for use.

Figure 5B:
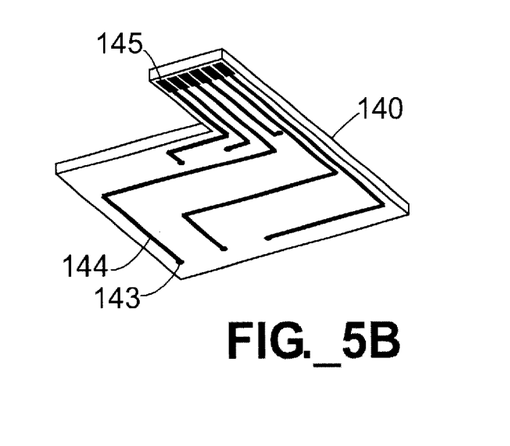
Figure 5C:
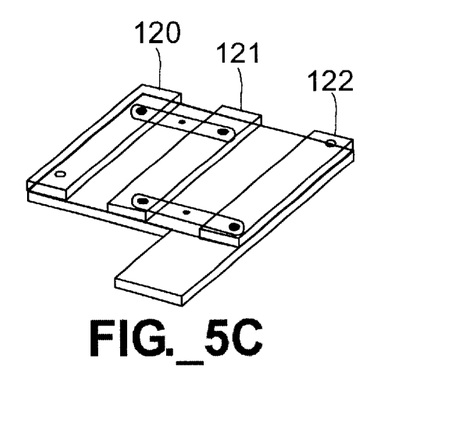

The assembled device is shown in FIG. 5B. In this example, fluid is injected into the inlet port 127 of device 122. The module 122 acts on the fluid to perform its function. The fluid then leaves the outlet port 128 and enters the channel 134 of the MCM. The fluid passes through channel 134 and enters module 121 at inlet port 126. Again, the module 121 performs its function and the fluid exits at port 125. The fluid enters the second MCM channel 133 and passes through into the inlet port 123 of the third module 120. The third module acts on the fluid and the fluid exits at exit port 124. The electrodes 141 within the MCM channels are used for a number of functions, including electrokinetic flow, electrophoresis, or electronic detection such as with a electrochemical detection or impedance measurements. The electrodes of the MCM can be connected to the outside world through an edge card connector, since the electrodes lead to plated pads 145 located on the back side of the, circuit board substrate. These pads are spaced with standard edge card spacing for convenient use.

The MCM is preferably used for continuous processing. Alternatively, once the microfluidic modules 120–122 have performed their function, one or all of the modules can be removed from the MCM. The modules can be reused in other configurations or discarded. The MCM can be reused with new modules or discarded.

If no electrode manipulation or testing is required, the circuit board substrate 140 can be replaced with a solid support. Alternatively, a flex-tape circuit board can be used for this embodiments so that the entire device is flexible.

The present invention described and claimed herein is not to be limited in scope by the specific embodiments herein disclosed, since these embodiments are intended merely to illustrate certain aspects of the invention. All equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The disclosures of all references cited herein are incorporated by reference in their entireties.

What is claimed is:

1. A microfluidic coupler comprising:

a first substrate layer;

a second substrate layer;

at least one stencil layer disposed between said first substrate layer and said second substrate layer, said stencil layer having a channel formed therein, wherein said channel has at least one dimension less than about 500 microns;

a first aperture in said first substrate layer or in said second substrate layer, wherein said first aperture is in fluid communication with said channel; and a second aperture in said first substrate layer or in said second substrate layer, wherein said second aperture is in fluid communication with said channel, wherein the first aperture can be used to connect the coupler to a first microfluidic device and the second aperture can be used to connect the coupler to a second microfluidic device.

2. The microfluidic coupler of claim 1 wherein the coupler is substantially planar.

3. The microfluidic coupler of claim 1 wherein the coupler is not planar.

4. The microfluidic device of claim 1 wherein said first and said second apertures are in said second substrate layer.

5. The microfluidic device of claim 4 wherein the outer surface of the second substrate layer is adhesive.

6. The microfluidic device of claim 1 wherein said first and said second apertures are in said first substrate layer.

7. The microfluidic device of claim 6 wherein the outer surface of the first substrate layer is adhesive.

8. The microfluidic device of claim 1 wherein the first aperture is in the first substrate layer and the second aperture is in the second substrate layer.

9. The microfluidic device of claim 8 wherein the outer surfaces of the first and second substrate layers are adhesive.

10. The microfluidic device of claim 1 wherein said device is flexible or malleable.

11. The microfluidic device of claim 1 wherein said substrate layers and said stencil layer are composed of materials selected from the group consisting of papers, foils and plastics.

12. The microfluidic device of claim 1 wherein said stencil layers are adhesive tapes.

13. The microfluidic device of claim 12 wherein said adhesive tapes are self-adhesive.

14. The microfluidic device of claim 13 wherein said tapes are selected from the group consisting of pressure curing tapes, heat curing, light curing tapes and chemically curing tapes.

15. The microfluidic device of claim 1 wherein said stencil layer is comprised of materials selected from the group consisting of polypropylenes, polytetrafluoroethylene, polycarbonates, polyesters, and polyimides.

16. A modular microfluidic system comprising:
a plurality of microfluidic modules,
wherein each module is self-contained for performing a desired function independently of each other module;
wherein the each module of the plurality of microfluidic modules has at least one fluid inlet and at least one fluid outlet; and
a plurality of multi-layer microfluidic couplers capable of rapid attachment to or detachment from at least two modules and adapted to communicate fluids between said at least two modules;
wherein at least one layer of each multi-layer microfluidic coupler is a channel-defining stencil layer.

17. The modular microfluidic system of claim 16 wherein any module of the plurality of microfluidic modules includes an etched silicon or glass substrate.

18. The modular microfluidic system of claim 16 wherein any module of the plurality of microfluidic modules includes a molded plastic, silicone or polymeric material.

19. The modular microfluidic system of claim 16 wherein any module of the plurality of microfluidic modules includes at least one stencil layer sandwiched between substrate layers.

20. The modular microfluidic system of claim 16 wherein any of the microfluidic modules is embossed.

21. The modular microfluidic system of claim 20 wherein the electrodes are connected by copper lines to plated pads.

22. The modular microfluidic system of claim 16 further comprising a base comprising a circuit board substrate.

23. The modular microfluidic system of claim 22 wherein the base further comprises electrodes corresponding to the inlet or outlet of at least one of the microfluidic modules.

24. The modular microfluidic system of claim 22 wherein the electrodes are used for electrokinetic flow.

25. The modular microfluidic system of claim 22 wherein the electrodes are used for electrophoresis.

26. The modular microfluidic system of claim 22 wherein the electrodes are used for electronic detection.

27. The modular microfluidic system of claim 16 wherein at least one of microfluidic modules is used for chemical or biochemical synthesis.

28. The modular microfluidic system of claim 16 wherein at least one of microfluidic modules is used for chemical or biochemical analysis.

29. A microfluidic device capable of fluidically coupling a first microfluidic module to a second microfluidic module, the device comprising:
a plurality of device layers defining a microfluidic channel having a first aperture and a second aperture;
wherein said channel has at least one dimension less than about 500 microns;
wherein the device is removably attached to the first microfluidic module and the second microfluidic module so that the first aperture is in fluid communication with the first microfluidic module and the second aperture is in fluid communication with the second microfluidic module.

30. The microfluidic device of claim 29 wherein the plurality of device layers includes at least one substantially planar stencil layer disposed between first substrate layer and a second substrate layer, wherein said channel is substantially within said stencil layer.

31. The microfluidic device of claim 30, wherein said first aperture and said second aperture are defined in said second substrate layer.

32. The microfluidic device of claim 31, wherein said second substrate layer defines a lower surface and said lower surface is adhesive.

33. The microfluidic device of claim 32, further comprising a backing layer.

34. The microfluidic device of claim 33, wherein said backing layer is a paper, a plastic or a metal foil.

35. The microfluidic device of claim 32, further comprising a backing layer removably adhered to the adhesive lower surface.

36. The microfluidic device of claim 30, wherein said substrate layers and said stencil layer are composed of materials selected from the group consisting of papers, foils and plastics.

37. The microfluidic device of claim 30, wherein said stencil layers are adhesive tapes.

38. The microfluidic device of claim 37, wherein said adhesive tapes are self-adhesive.

39. The microfluidic device of claim 38, wherein said tapes are selected from the group consisting of pressure curing tapes, heat curing, light curing tapes and chemically curing tapes.

40. The microfluidic device of claim 37, wherein said stencil layers are comprised of materials selected from the group consisting of polypropylenes, polytetrafluoroethylene, polycarbonates, polyesters, and polyimides.

41. The microfluidic device of claim 30, wherein said first substrate layer is semipermeable, allowing gases to pass, but not allowing liquid to pass.

42. The microfluidic device of claim 41, wherein said first aperture is in said second substrate layer.

43. The microfluidic device of claim 29, wherein said device is flexible or malleable.

44. The microfluidic device of claim 29, further comprising a semipermeable membrane covering said second aperture, said semipermeable membrane allowing gases to pass, but not allowing liquid to pass.

45. The microfluidic device of claim 44, wherein said semipermeable membrane has a pore size of less than about 75 microns.

46. The microfluidic device of claim 29, further comprising an inlet port in fluid communication with said first aperture.

47. The microfluidic device of claim 46, wherein said inlet port can mate with a syringe or a tube.

48. The microfluidic device of claim 29 wherein the channel is derivatized with a chemical or biological moiety.

49. The microfluidic device of claim 48, wherein the channel is derivatized using a silanization reaction.

* * * * *

UNITED STATES PATENT AND TRADEMARK OFFICE
CERTIFICATE OF CORRECTION

PATENT NO.   : 6,536,477 B1
DATED        : Mach 25, 2003
INVENTOR(S)  : O'Connor, Stephen D. et al.

It is certified that error appears in the above-identified patent and that said Letters Patent is hereby corrected as shown below:

<u>Column 4,</u>
Line 8, the phrase "couple the microfluidic.coupler to the microfluidic device is" should read -- couple the microfluidic coupler to the microfluidic device is --

<u>Column 5,</u>
Lines 62 and 63, the phrase "provides for modular microfluidic system" should read -- provides for a modular microfluidic system --

<u>Column 10,</u>
Lines 17 and 18, the phrase "can be used for this" should read -- can be used for these --

Signed and Sealed this

Twenty-second Day of June, 2004

JON W. DUDAS
*Acting Director of the United States Patent and Trademark Office*